(12) United States Patent
Shin et al.

(10) Patent No.: US 10,806,612 B2
(45) Date of Patent: Oct. 20, 2020

(54) METHOD FOR MANUFACTURING STENT USING SHAPE MEMORY ALLOY WIRE, STENT MANUFACTURED THEREBY, AND JIG FOR MANUFACTURING SAME

(71) Applicants: TAEWOONG MEDICAL CO., LTD., Gyeonggi-do (KR); Kyong Min Shin, Gyeonggi-do (KR)

(72) Inventors: Kyong Min Shin, Gyeonggi-do (KR); Young Ill Hong, Gyeonggi-do (KR); Se Ik Park, Seoul (KR)

(73) Assignees: TAEWOONG MEDICAL CO., LTD., Gyeonggi-do (KR); Kyoung Min Shin, Gyeonggi-do (KR)

( * ) Notice: Subject to any disclaimer, the term of this patent is extended or adjusted under 35 U.S.C. 154(b) by 199 days.

(21) Appl. No.: 16/077,633

(22) PCT Filed: Feb. 9, 2017

(86) PCT No.: PCT/KR2017/001401
§ 371 (c)(1),
(2) Date: Aug. 13, 2018

(87) PCT Pub. No.: WO2017/142253
PCT Pub. Date: Aug. 24, 2017

(65) Prior Publication Data
US 2019/0053926 A1 Feb. 21, 2019

(30) Foreign Application Priority Data
Feb. 15, 2016 (KR) .......................... 10-2016-0017142

(51) Int. Cl.
*A61F 2/90* (2013.01)
*B21F 45/00* (2006.01)
*B21F 1/00* (2006.01)

(52) U.S. Cl.
CPC .................. *A61F 2/90* (2013.01); *B21F 1/00* (2013.01); *B21F 45/008* (2013.01);
(Continued)

(58) Field of Classification Search
CPC ...... A61F 2/86; A61F 2/90; A61F 2210/0014; A61F 2220/0083; A61F 2240/00;
(Continued)

(56) References Cited

FOREIGN PATENT DOCUMENTS

| KR | 1020020078129 | 10/2002 |
|---|---|---|
| KR | 100457629 | 11/2004 |

(Continued)

*Primary Examiner* — Christopher D. Prone
*Assistant Examiner* — Tiffany P Shipmon
(74) *Attorney, Agent, or Firm* — IP & T Group LLP

(57) ABSTRACT

The present invention relates to a stent that uses a shape memory alloy wire, the stent being an expansion device installed on a part of a body lumen, which is constricted, or which has been constricted, so as to widen the passage of the lumen in response to the lesion part. The purpose of the present invention is to provide a method for manufacturing a stent using a shape memory alloy wire such that the stent maintains a high degree of conformability in a bent portion of a body lumen in which the same is inserted while substantially improving rigidness and durability against continuously applied fatigue, a stent manufactured thereby, and a jig for manufacturing the same.

18 Claims, 11 Drawing Sheets

(52) U.S. Cl.
CPC ................ *A61F 2210/0014* (2013.01); *A61F 2220/0083* (2013.01); *A61F 2240/00* (2013.01); *A61F 2240/001* (2013.01)

(58) Field of Classification Search
CPC .... A61F 2240/001; B21F 1/00; B21F 45/008; D03D 3/06; D03D 3/02; D03D 1/0005; D10B 2401/10; D10B 2509/06
See application file for complete search history.

(56) References Cited

FOREIGN PATENT DOCUMENTS

| | | |
|---|---|---|
| KR | 100457630 | 11/2004 |
| KR | 100633020 | 10/2006 |
| KR | 1020090038209 | 4/2009 |
| KR | 101021615 | 3/2011 |
| KR | 1020110064090 | 6/2011 |
| KR | 101109709 | 1/2012 |

METHOD FOR MANUFACTURING STENT USING SHAPE MEMORY ALLOY WIRE, STENT MANUFACTURED THEREBY, AND JIG FOR MANUFACTURING SAME

This application is a national stage application of PCT/KR2017/001401 filed on Feb. 9, 2017, which claims priority of Korean patent application number 10-2016-0017142 filed on Feb. 15, 2016. The disclosure of each of the foregoing applications is incorporated herein by reference in its entirety.

TECHNICAL FIELD

The present invention relates generally to a method for manufacturing a stent using a shape memory alloy wire, a stent manufactured thereby, and a structure of a jig for manufacturing the same, the stent being an expansion device installed at an on-going stenosis site or stenosis site of a body lumen so as to widen the passage of the lumen to cope with a lesion site. More particularly, the present invention relates to a method for manufacturing a stent using a shape memory alloy wire, a stent manufactured thereby, and a jig for manufacturing the same, in which rigidity and resistance of the stent to continuous fatigue are greatly improved while a high degree of conformability is maintained at a bent portion of the body lumen in which the stent is inserted.

BACKGROUND ART

A stent using a shape memory alloy has been disclosed in various forms, and the stent is known as an expansion mechanism configured to have elasticity in the radial direction and the longitudinal direction to always return to the initial state unless it is forcibly suppressed by the external force, so as to enlarge the passage of the stenosis site of the body lumen.

To be more specific to the stent, there is a known stent configured to have a body by perforating a space for a part of a plate of shape memory alloy material and bending the same in a cylindrical shape so as to maintain the expanded shape, and the plate bending type stent has a strong mechanical resistance but deformability thereof due to its own shrinkage is very low and it is hardly used because it is difficult to insert and remove.

To solve the problem of the above stent, there has been disclosed a stent configured such that a superelastic shape memory alloy wire is interlocked to form a hollow cylindrical body having a predetermined length so as to have a rhombus-shaped space, and opposite ends thereof are connected by welding.

The wire type stent is suitable and easy to reduce the volume of the hollow cylindrical body during the procedure, and the stent having a reduced volume is inserted into the lesion site of the blood vessel as an introducer and is used to push the lesion outward to expand the lumen such as the blood vessel.

Hereinafter, a structure of a wire type and problems thereof will be described.

The initial wire type stent is configured such that by using a shape memory alloy wire, two intersecting wires are vertically and horizontally staggered to form rhombus shape cells, in which each cell mutually supports each other to maintain a cylindrical tube (referred to as prior art 1).

As another stent, which has been disclosed in the document of the applicant's Patent No. 457629 (referred to as prior art 2), it is configured such that a first wire and a second wire of superelastic shape memory alloy material are cross-bent at different positions so as to have a diagonal length of l (a length of a diagonal line of the jig for manufacturing an expansion mechanism described later, when the wire is hooked to a projecting pin at one position) and a diagonal length of 2 μl in the circumferential direction, and includes rhombus-shaped spaces that vary as each wire crosses from top to bottom and from bottom to top, staggered portions where each wire is staggered at different positions to be able to contract in the longitudinal direction, and intersection straight line portions having a repulsive force against the longitudinal contraction and being partially provided between the same circumferential direction and the staggered portions in the longitudinal direction, thereby providing a variable state holding type expansion mechanism.

Further, in the document of the applicant's Patent No. 457630 (referred to as prior art 3), there has been disclosed a variable state holding type expansion mechanism configured such that by separately using a first wire and a second wire of superelastic shape memory alloy material, a first expansion mechanism forms variable rhombus-shaped spaces by a first wire of superelastic shape memory alloy material being bent and crossed from top to bottom or from bottom to top to form staggered portions contractible in the longitudinal direction by being staggered at different positions from intersection straight line portions, so as to have a repulsive force against the longitudinal contraction, and a second expansion mechanism is configured such that a second wire is diagonally moved through the upper portion or lower portion of the first wire along the top and bottom of the first wire in parallel with the first wire installed, whereby each of the variable rhombus-shaped spaces formed by the first cylindrical expansion mechanism is evenly divided into quarters by the second cylindrical expansion mechanism, and the tow expansion mechanisms are prevented from being separated from each other while being operated.

The staggered portions are referred to as "hooks" because they have a structure in which wires traveling in different directions are interlocked together and travel in different directions, and are configured and function so that the stent maintains the same shape without resistance at the bent portion of the lumen.

Further, in the document of the applicant's Patent No. 1109709 (referred to as prior art 4), there has been disclosed a stent configured such that lengths of sides of two adjacent pairs of each rhombus-shaped cells of the prior arts 2 and 3 are equal to each other to form a rectangular shape with "hooks" provided, thereby minimizing loops or intersections located in the circumferential direction while having two sufficient resistance along the circumferential direction with respect to a lesion site, so as to minimize the diameter of the tube to be inserted when the stent of the present invention is inserted into an insertion device, whereby it can be easily used for the lumen even with a small diameter.

However, the stent of the prior art 1 is problematic in that since all the stent cells are connected, the lumen cannot maintain the bending of the lumen and the conformability which is not resisting the peristaltic motion of the lumen is lowered because it is unconditionally expanded by a predetermined length, especially at the bending lumen site.

The prior arts 2 to 4 are configured to be connected through hooks to a part of the cells, which was not present in the prior art 1, thereby improving conformability, but in the case of prior art 2, there is a problem that the stent deployment is insufficient after inserting into the lumen, and there is a problem in meeting the market situation requiring a stent having a stronger force while reducing the profile of the stuck stent to be inserted and performed in the introducer.

Further, in the case of prior arts 3 and 4, although they have been attempted to solve the problem of prior art 2, a result of the test with a multi-axial stent fatigue test instrument has been found that they are vulnerable to swelling and bending fatigue.

In other words, in the case of prior art 3, it is vulnerable to the deploy force, in the case of prior art 3, the bending fatigue is insufficient, and in the case of prior art 4, it is vulnerable to the expansion fatigue.

As a result, it can be seen that the inventions of the prior arts 1 to 4 have various advantages, but have different inherent disadvantages.

DISCLOSURE

Technical Problem

Accordingly, the present invention has been made keeping in mind the above problems occurring in the conventional stent configured by interconnecting a wire of shape memory alloy material with a hook and a cell structure, and it is intended to solve the following problems.

The present invention provides a method for manufacturing stent using shape memory alloy wire, stent manufactured thereby, and jig for manufacturing same, in which the resistance to repeated expansion and contraction is greatly improved by double cells in which one cell forming a rhombic geometry is overlapped asymmetrically with another cell, and early disconnection can be prevented by dispersing the concentration of stress.

The present invention provides a method for manufacturing stent using shape memory alloy wire, stent manufactured thereby, and jig for manufacturing same, in which the profile of the stuck stent is small to be installed in the introducer while maintaining the conformability of the conventional stent, whereby the stent has a low deployment value and expandable with a small deploy force.

The present invention provides a method for manufacturing stent using shape memory alloy wire, stent manufactured thereby, and jig for manufacturing same, in which it is easy and flexible to use an introducer because it is possible to use a small introducer for the same force or a stent with a stronger force for the same introducer.

The present invention provides a method for manufacturing a stent using shape memory alloy wire, a stent manufactured thereby, and a jig for manufacturing same, in which the stent has good mechanical resistance to fatigue that occurs continuously in the lumen.

The present invention provides a method for manufacturing a stent using shape memory alloy wire, a stent manufactured thereby, and a jig for manufacturing same, in which the profile of the stuck stent is further reduced by uniformly distributing the arrangement of the hooks not to be linearly concentrated in a horizontal or vertical direction (on the same line), whereby it is easy to install the stent in the introducer.

The present invention provides a method for manufacturing a stent using shape memory alloy wire, a stent manufactured thereby, and a jig for manufacturing same, in which the friction between the introducer and the outer circumference of the introducer is minimized due to ease of installing in the introducer, thereby reducing the deploy force and being useful for the success of the procedure.

The present invention provides a method for manufacturing a stent using shape memory alloy wire, a stent manufactured thereby, and a jig for manufacturing same, in which it is possible to increase productivity by simplifying the interconnecting of stent wires.

Technical Solution

In order to achieve the above object, the present invention is formed in a rhombus shape based on a unit cell, and is configured such that the horizontal diagonal distance Ph and the vertical diagonal distance Pv of the unit cell are in one of the relations Ph=Pv, Ph<Pv, and Ph>Pv, and the unit cell is continuously repeated by interconnecting the stent wire, thereby forming a first stent having a predetermined circumference and a length, and the unit cell is vertically spaced downward by the offset pitch Pv2 such that a second stent having the same predetermined circumference and length is overlapped with the first stent, whereby two sides provided at equiangular positions of the overlapped first and second stents are spaced by the offset pitch Pv2, and a geometrically wide overlapping space is formed by the overlapping.

The offset pitch Pv2 may be formed to be less than at least 1/2Pv.

The first wire forming the first stent may include: a plurality of bent loops with uppermost and lowermost ends thereof being curved; a first pattern portion 1 connecting from any one origin of the uppermost portion to the lowermost portion of the first stent to form a plurality of rhombic spaces; a second pattern portion directing from an end point of the first pattern portion to an upward direction; and a third pattern portion, a fourth pattern portion, a fifth pattern portion, and a sixth pattern portion directing from the second pattern portion to an upward direction, sequentially, whereby the interconnection of wire is implemented.

The second wire forming the second stent may include: a plurality of bent loops with uppermost and lowermost ends of the second stent being curved starting from an origin shifted downward by being spaced by the offset pitch Pv2 from the origin of the first stent; a first a pattern portion connecting from the shifted origin to the lowermost portion of the second stent to form a plurality of rhombic spaces; a second a pattern portion directing from an end point of the first a pattern portion to an upward direction; and a third a pattern portion, a fourth a pattern portion, a fifth a pattern portion, and a sixth a pattern portion directing from the second a pattern portion to an upward direction, sequentially, whereby by interconnecting wire, the second stent is spaced apart from the first stent by the offset pitch Pv2 and is overlapped with the same.

The first pattern portion may be shifted downward from the origin by a diagonal distance 2L corresponding to the horizontal and vertical diagonal distances Ph and Pv, and bent diagonally upward by a diagonal distance L of one side of the unit cell, and interconnected to the lower most end point vertically extending from the origin of the first stent by repeating the diagonal distances 2L and L.

The second pattern portion may be manufactured by the following steps: repeating upward and downward on the same horizontal axis by the diagonal distance L of one side of the unit cell based on the end point of the first pattern portion as a starting point; and when section of the diagonal distance 2L of the first pattern portion 1 is encountered, crossing upward by the diagonal distance 2L and interconnecting to an end point.

The third pattern portion may be manufactured by the following steps: repeating upward and downward on the same horizontal axis by the diagonal distance L of one side of the unit cell based on the end point of the second pattern portion as a starting point; and when section of the diagonal distance 2L of the first pattern portion is encountered, crossing upward by the diagonal distance 2L and moving to a horizontal axis located one level above the horizontal axis and repeating upward and downward on the same horizontal axis, thereby interconnecting to the end point.

The fourth pattern portion may be manufactured by the following steps: repeating upward and downward on the same horizontal axis by the diagonal distance L of one side of the unit cell based on the end point of the third pattern portion as a starting point; and when section of the diagonal distance 2L of the first pattern portion 1 is encountered, crossing upward by the diagonal distance 2L and moving to a horizontal axis located one level above the horizontal axis, and repeating upward and downward on the same horizontal axis, thereby interconnecting to the end point.

The fifth pattern portion may be manufactured by the following steps: repeating upward and downward on the same horizontal axis by the diagonal distance L of one side of the unit cell based on the end point of the fourth pattern portion as a starting point; and when section of the diagonal distance 2L of the first pattern portion is encountered, crossing upward by the diagonal distance 2L and moving to a horizontal axis located one level above the horizontal axis, and repeating upward and downward on the same horizontal axis, thereby interconnecting to the end point.

The sixth pattern portion may be manufactured by the following steps: based on the end point of the fifth pattern portion as a starting point, when section of the diagonal distance 2L of the first pattern portion is encountered, crossing upward by the diagonal distance 2L; and repeating upward and downward on the same horizontal axis by the diagonal distance L of one side of the unit cell; and interconnecting to return to the origin.

The upper portion of the sixth pattern portion may be on the same horizontal axis as the starting origin of the first pattern portion, and be completed by connecting end portions of the wire after interconnecting the wire of the first stent.

The interconnection pattern portion of the wire of the second stent may be the same as that of the wire of the first stent, and only the starting origin of the second stent may be the shifted origin at a location shifted downward by the offset pitch Pv2 from the starting origin of the first stent.

The starting point of each pattern may be from the origin of the wire of the first stent to the end point of the vertically extending position from the origin, and the end point may become the starting point of another continuous pattern.

Advantageous Effects

According to the present invention, it is advantageous in that the resistance to repeated expansion and contraction is greatly improved by double cells in which one cell forming a rhombic geometry is overlapped asymmetrically with another cell, and early disconnection can be prevented by dispersing the concentration of stress, and since the profile of the stuck stent is small to be installed in the introducer while maintaining the conformability of the conventional stent, the stent has a low deployment value and expandable with a small deployment force.

According to the present invention, it is further advantageous in that it is easy and flexible to use an introducer because it is possible to use a small introducer for the same force or a stent with a stronger force for the same introducer, the stent has good mechanical resistance to fatigue that occurs continuously in the lumen, the profile of the stuck stent is further reduced by uniformly distributing the arrangement of the hooks not to be linearly concentrated in a horizontal or vertical direction (on the same line), whereby it is easy to install the stent in the introducer, the friction between the introducer and the outer circumference of the introducer is minimized due to ease of installing in the introducer, thereby reducing the deployment force and being useful for the success of the procedure, and it is possible to increase productivity by simplifying the interconnecting of stent wires.

According to the present invention, it is further advantageous in that since double cells are spaced by an offset pitch and can be manufactured by increasing or decreasing the offset pitch, it is easily deformed according to the application.

DESCRIPTION OF DRAWINGS

FIG. 3 is an interconnection diagram showing a first pattern portion;

FIG. 4 is an interconnection diagram showing a second pattern portion;

FIG. 5 is an interconnection diagram showing a third pattern portion;

FIG. 6 is an interconnection diagram showing a fourth pattern portion;

FIG. 7 is an interconnection diagram showing a fifth pattern portion;

FIG. 8 is a pattern diagram showing the first stent with interconnection completed, as an interconnection diagram showing a sixth pattern portion;

BEST MODE

Hereinafter, various embodiments of the present invention will be described with reference to the accompanying drawings.

As a basic embodiment, which is shown and described first, a mesh wire stent, which is configured such that a circumferential surface of the stent is equally divided into 14 parts, from A1 to A14, and is longitudinally divided into from B1 to B14 and the same is interconnected.

Figure 1:
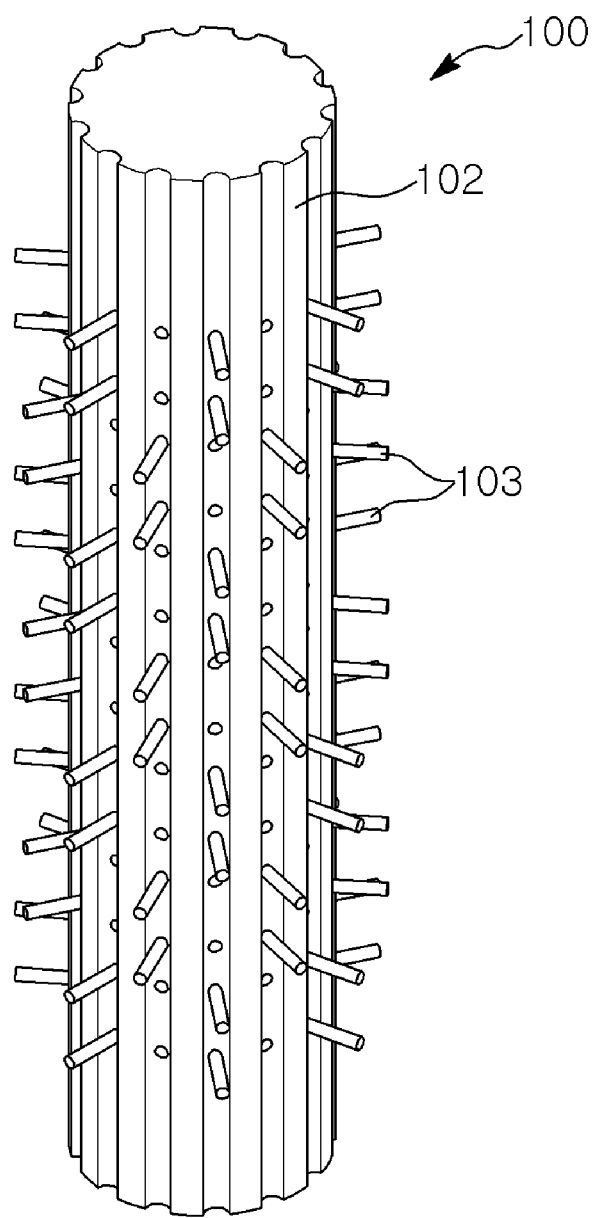
FIG. 1 is an external configuration diagram showing a jig for manufacturing a stent of the present invention.
Figure 2:
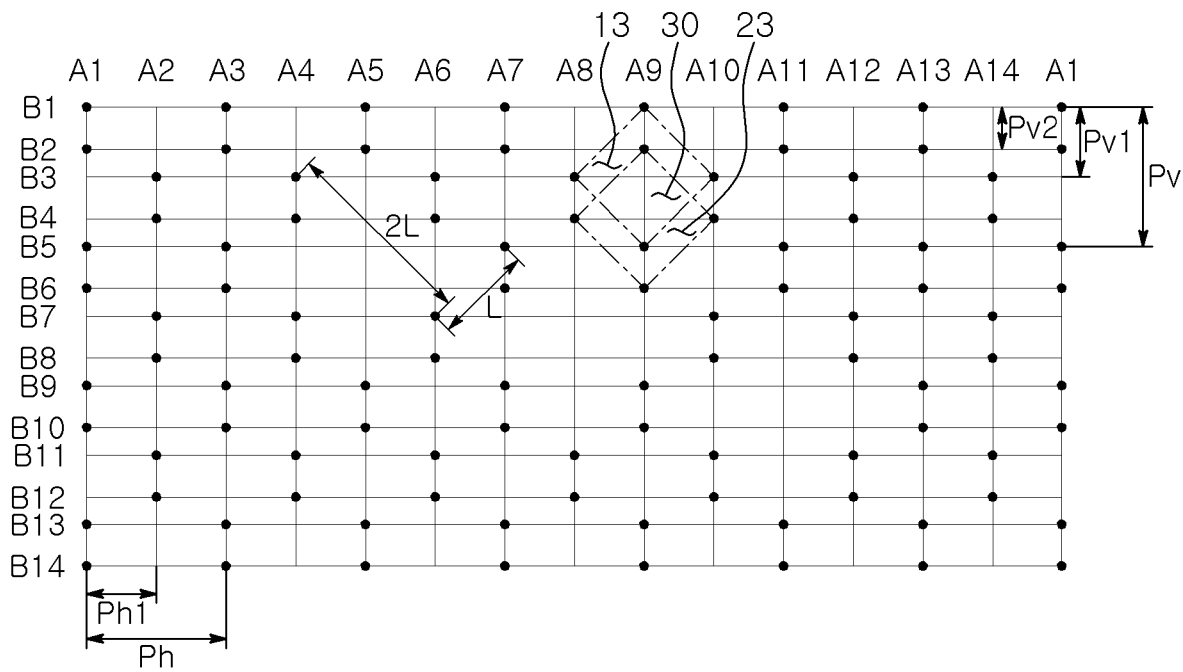
FIG. 2 is a deployment view showing a jig of the present invention.
Figure 3:
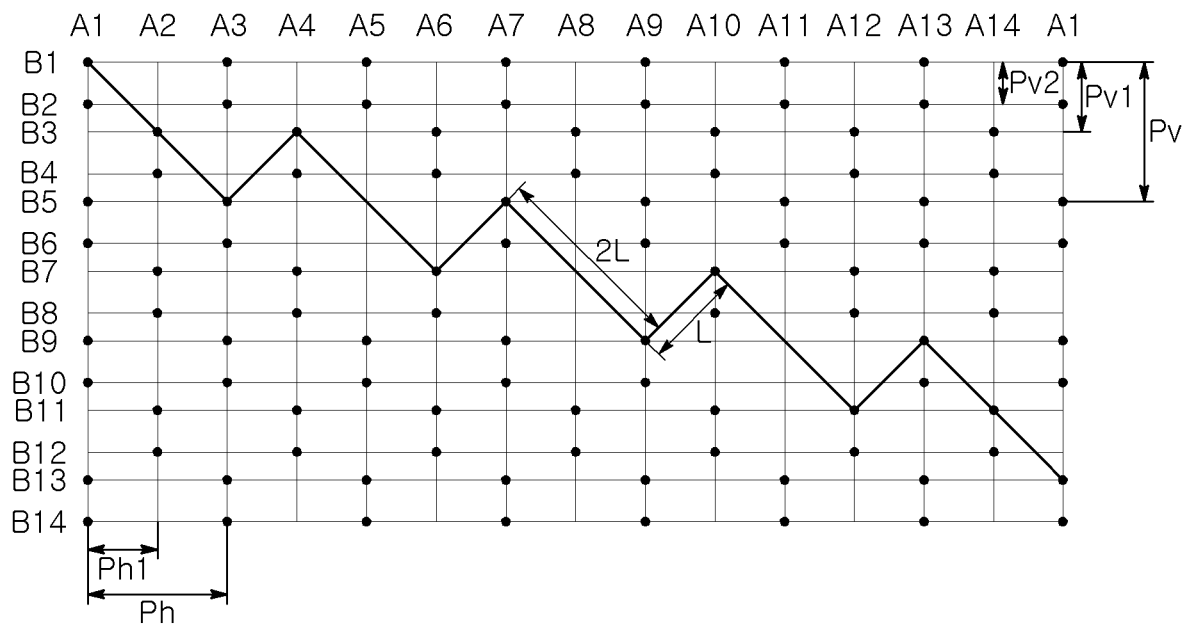
FIGS. 3 to 8 are pattern diagrams showing a pattern portion of a first wire for manufacturing a first stent, as an embodiment of the present invention.
Figure 4:
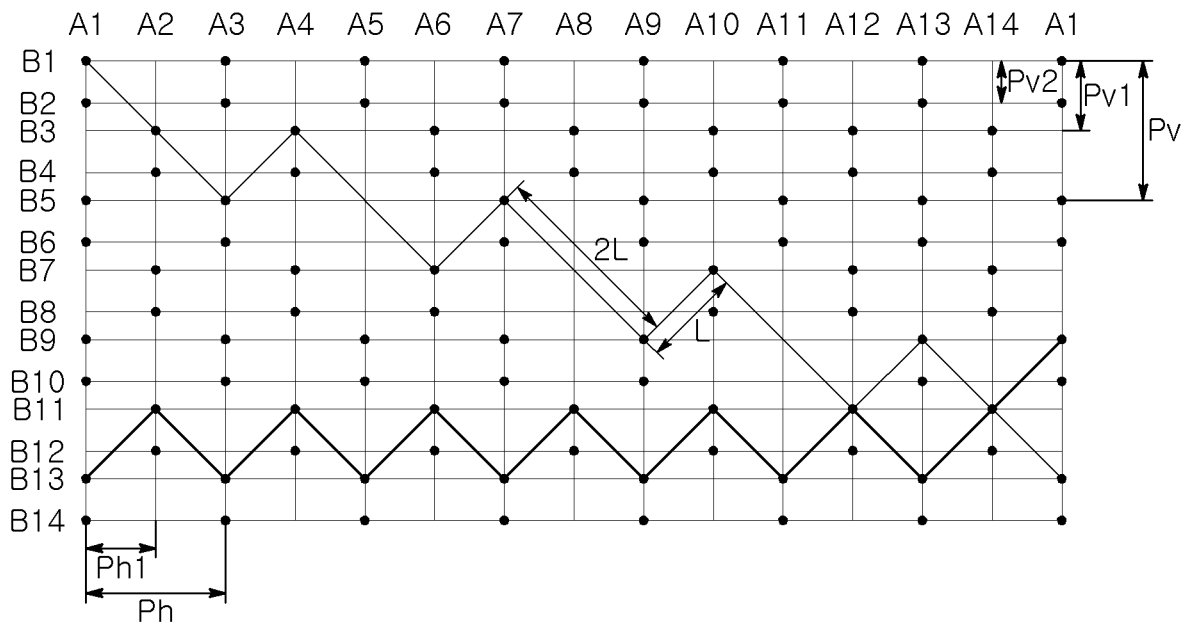
Figure 5:
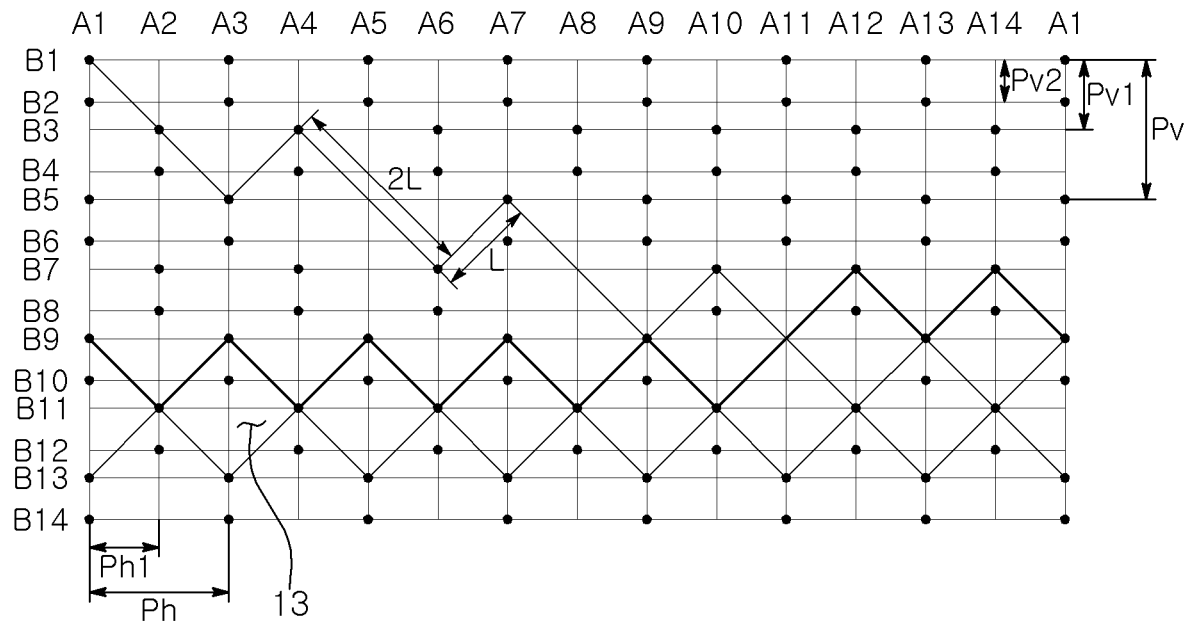
Figure 6:
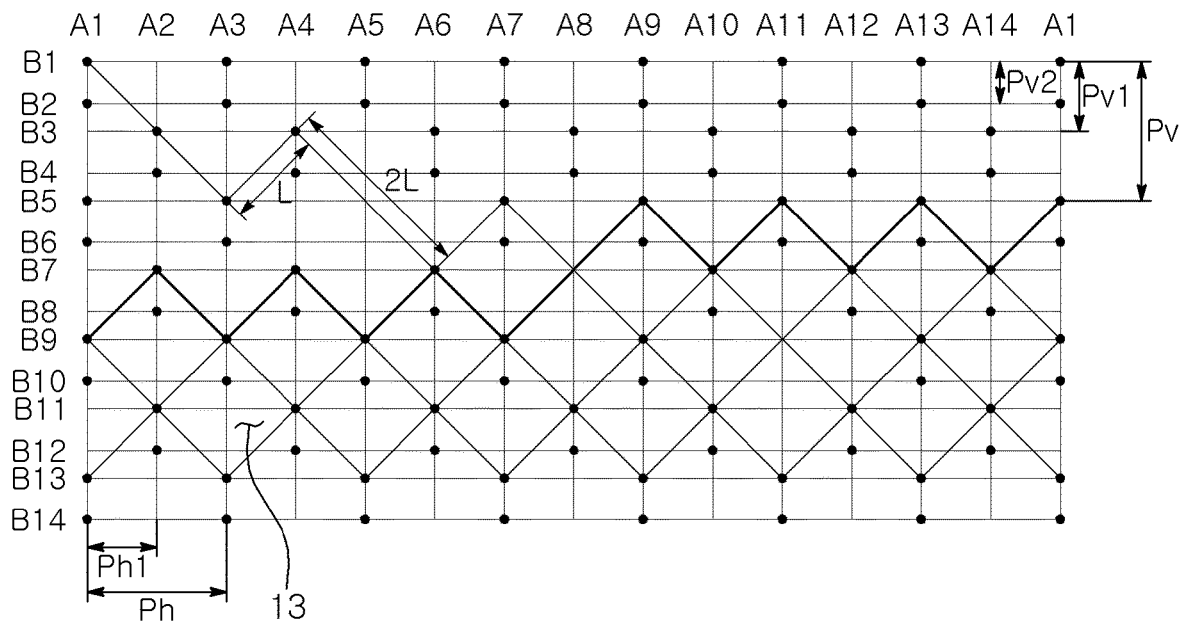
Figure 7:
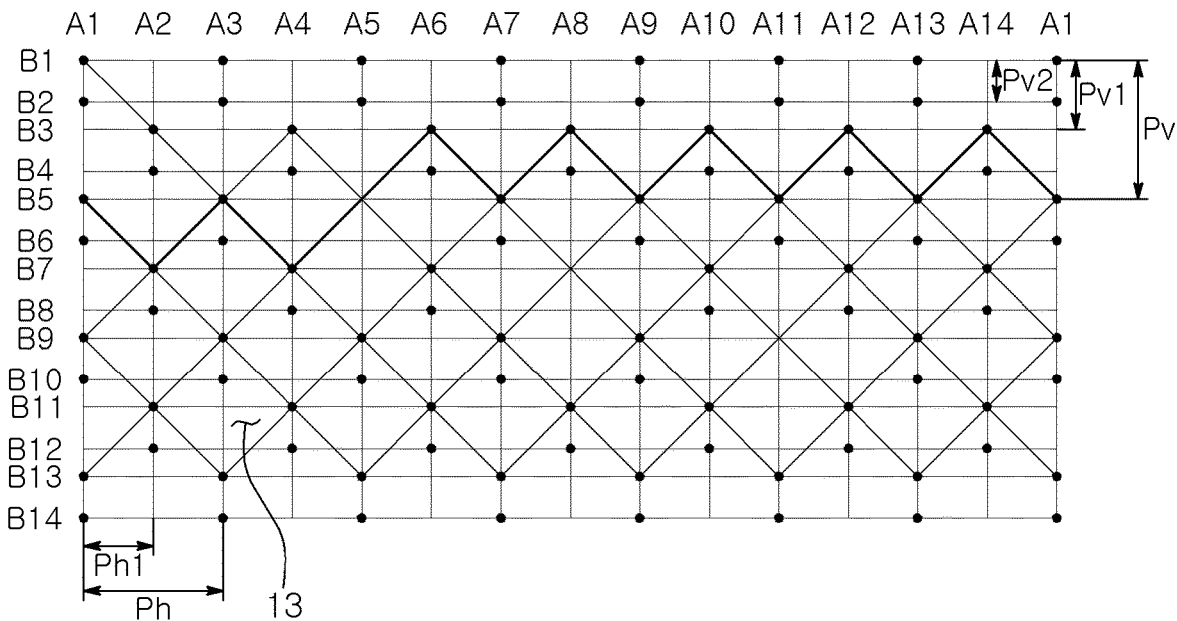
Figure 8:
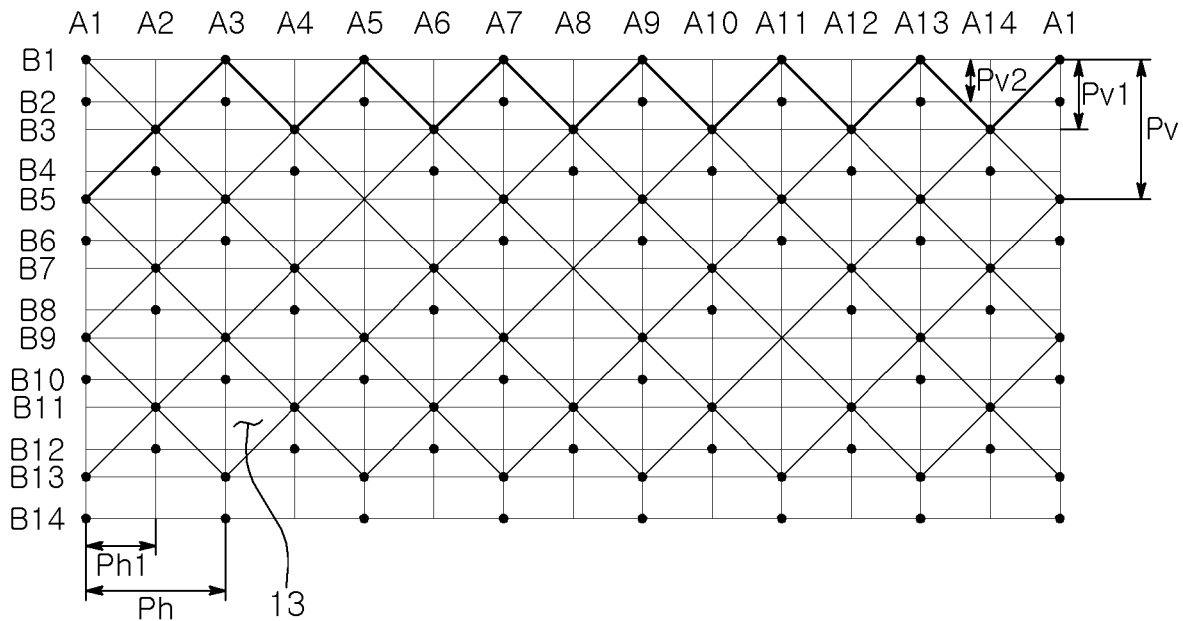
Figure 9:
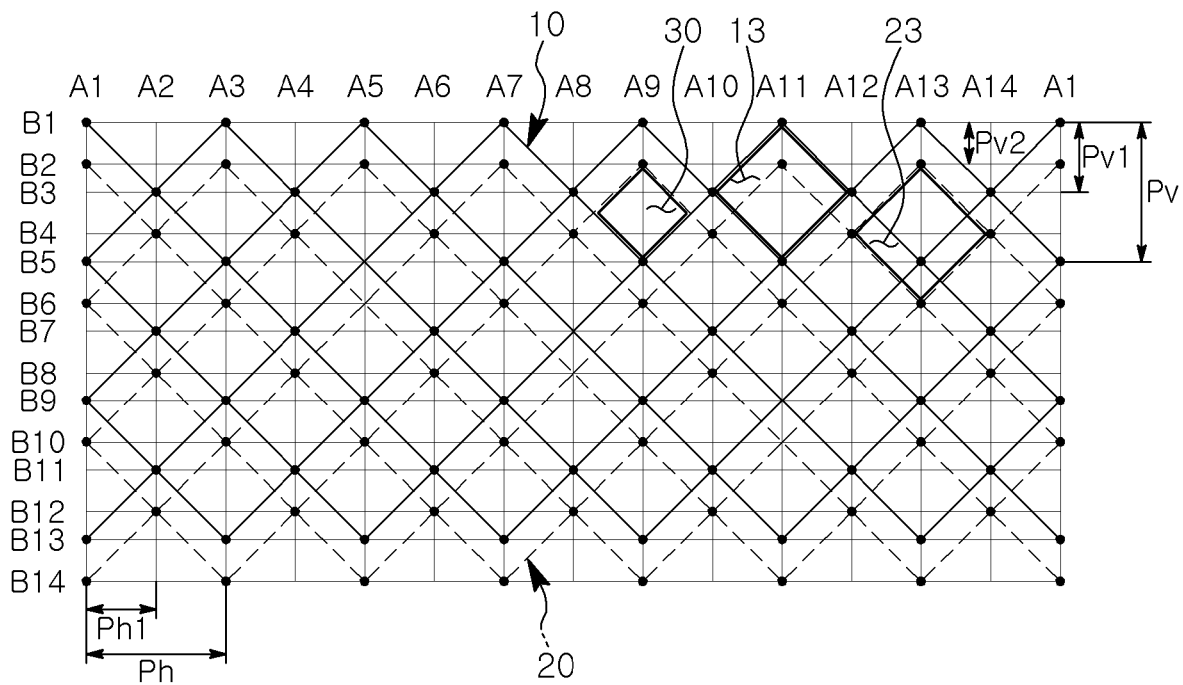
FIG. 9 is a pattern diagram showing a state in which interconnection is completed by overlapping the second stent with the first stent of the present invention.

As shown in FIGS. 1 to 2, in a stent of the present invention, which is interconnected by using a shape memory alloy wire, a jig 100 is constituted by a body 102, and detachable pins 103.

The jig 100 has a circumference forming a hollow part of a stent to be manufactured, and is formed in a vertically long cylindrical shape. More particularly, it is formed in a cylindrical rod extended beyond the uppermost position and the lowermost position of the split, in which the circumference is equally divided into 14 parts, and the circumference is longitudinally divided into 14 parts while being perpendicular to a vertical line extending from each equally divided position in the longitudinal direction.

To describe a method from manufacturing the stent of the present invention, when the jig is developed equivalently, it can be seen as in FIG. 2.

The X-axis shown in FIG. 2 refers to the circumferential surface of the jig, and the Y-axis refers to the longitudinal direction, wherein at a part of intersections between equator lines A1 to A14 of the circumferential surface and circumferential dividing lines B1 to B14 in the longitudinal direction, a pin 3 is inserted to change the direction of the interconnecting wire and to hook the interconnecting wire with the crossing interconnecting wire.

The equator lines A1, A3, A5, A7, A9, A11, and A13 are divided by being spaced by a horizontal diagonal distance Ph of a cell forming a rhombic geometry in the X-axis direction from an arbitrary selected origin on the circumferential surface of the jig, and the equator lines A2, A4, A6, A8, A10, A12, and A14 are divided by being spaced by the horizontal diagonal distance Ph at locations apart by a length Ph1 bisecting the equator line, thereby forming 14 equator lines A1 to A14.

In the longitudinal direction of the jig, the dividing lines B3, B5, B7, B9, B11, and B13 are divided by being spaced by a length Pv1 bisecting the dividing line B1, which is the reference in the Y-axis direction from the origin, and a vertical diagonal distance Pv of a cell forming a rhombic geometry from the dividing line B1, and the dividing lines B2, B4, B6, B8, B10, B12, and B14 are divided into the same number of the dividing lines B1, B3, B5, B7, B9, B11, and B13 at locations apart by an offset pitch Pv2 from the dividing line B1, thereby forming 14 dividing lines B1 to B14.

When the horizontal diagonal distance Ph and the vertical diagonal distance Pv are in a relation of Ph=Pv, a rhombus shape is formed, interior angles of which are right angles and the length is Ph1=Pv1.

Each of the equator lines and the dividing lines is a virtual line, and some of the intersections are formed with a hole through which the pin 3 is inserted, wherein the colored circle in FIG. 2 shows the pin, and in the description for interconnecting the stent wire, the intersection of each line is described by the coordinates of the combination of the lines.

In the equivalent diagram, the redundant equator lines A1 shown on the left and right sides in the circumference equator lines in the X-axis direction are the same equator line, which is deployed for illustrative purposes, and the equator line A1 on the right is not real and is a reference line to help understanding.

A method for manufacturing stent using shape memory alloy wire of the present invention will be described with reference to FIGS. 3 to 9.

The present invention is formed in a rhombus shape based on a unit cell, and is configured such that the horizontal diagonal distance Ph and the vertical diagonal distance Pv of the unit cell are in one of the relations Ph=Pv, Ph<Pv, and Ph>Pv, and the unit cell is continuously repeated by interconnecting the stent wire, thereby forming a first stent 10 having a predetermined circumference and a length, and the unit cell is vertically spaced downward by the offset pitch Pv2 such that a second stent 20 having the same predetermined circumference and length is overlapped with the first stent, whereby two sides provided at equiangular positions of the overlapped first and second stents 10 and 20 are spaced by the offset pitch Pv2, and a geometrically wide overlapping space 30 is formed by the overlapping.

The offset pitch Pv2 is formed to be less than at least 1/2Pv.

The first wire forming the first stent 10 includes: a plurality of bent loops 40 with uppermost and lowermost ends thereof being curved; a first pattern portion 1 connecting from any one origin (A1, B1) of the uppermost portion to the lowermost portion of the first stent to form a plurality of rhombic spaces 13; a second pattern portion 2 directing from an end point (A1, B13) of the first pattern portion 1 to upward direction; and a third pattern portion 3 a fourth pattern portion 4, a fifth pattern portion 5, and a sixth pattern portion 6 directing from the second pattern portion 2 to upward direction, sequentially, whereby the interconnection of wire is implemented.

The second wire forming the second stent 20 includes: a plurality of bent loops 40 with uppermost and lowermost ends of the second stent being curved starting from an origin (A1, B2) shifted downward by being spaced by the offset pitch Pv2 from the origin of the first stent 10; a first a pattern portion 1a connecting from the shifted origin to the lowermost portion of the second stent to form a plurality of rhombic spaces 23; a second a pattern portion 2a directing from an end point of the first a pattern portion 1a to upward direction; and a third a pattern portion 3a, a fourth a pattern portion 4a, a fifth a pattern portion 5a, and a sixth a pattern portion 6a directing from the second a pattern portion to upward direction, sequentially, whereby by interconnecting wire, the second stent is spaced apart from the first stent 10 by the offset pitch Pv2 and is overlapped with the same.

The first pattern portion 1 is shifted downward from the origin by a diagonal distance 2L corresponding to the horizontal and vertical diagonal distances Ph and Pv, and is bent diagonally upward by a diagonal distance L of one side of the unit cell, and is interconnected to the lower most end point (A1, B13) vertically extending from the origin (A1, B1) of the first stent by repeating the diagonal distances 2L and L.

The second pattern portion 2 is manufactured by the following steps: repeating upward and downward on the same horizontal axis by the diagonal distance L of one side of the unit cell based on the end point (A1, B13) of the first pattern portion as a starting point; and when section of the diagonal distance 2L of the first pattern portion 1 is encountered, crossing upward by the diagonal distance 2L and interconnecting to an end point (A1, B9).

The third pattern portion 3 is manufactured by the following steps: repeating upward and downward on the same horizontal axis by the diagonal distance L of one side of the unit cell based on the end point (A1, B9) of the second pattern portion as a starting point; and when section of the diagonal distance 2L of the first pattern portion 1 is encountered, crossing upward by the diagonal distance 2L and moving to a horizontal axis located one level above the horizontal axis and repeating upward and downward on the same horizontal axis, thereby interconnecting to the end point (A1, B9).

The fourth pattern portion 4 is manufactured by the following steps: repeating upward and downward on the same horizontal axis by the diagonal distance L of one side of the unit cell based on the end point (A1, B9) of the third pattern portion as a starting point; and when section of the diagonal distance 2L of the first pattern portion 1 is encountered, crossing upward by the diagonal distance 2L and moving to a horizontal axis located one level above the horizontal axis, and repeating upward and downward on the same horizontal axis, thereby interconnecting to the end point (A1, B5).

The fifth pattern portion 5 is manufactured by the following steps: repeating upward and downward on the same horizontal axis by the diagonal distance L of one side of the unit cell based on the end point (A1, B5) of the fourth pattern portion as a starting point; and when section of the diagonal distance 2L of the first pattern portion is encountered, crossing upward by the diagonal distance 2L and moving to a horizontal axis located one level above the horizontal axis, and repeating upward and downward on the same horizontal axis, thereby interconnecting to the end point (A1, B5).

The sixth pattern portion 6 is manufactured by the following steps: based on the end point (A1, B5) of the fifth pattern portion as a starting point, when section of the diagonal distance 2L of the first pattern portion 1 is encountered, crossing upward by the diagonal distance 2L; and repeating upward and downward on the same horizontal axis by the diagonal distance L of one side of the unit cell; and interconnecting to return to the origin (A1, B1).

The upper portion of the sixth pattern portion 6 is on the same horizontal axis as the starting origin of the first pattern portion 1, and is completed by connecting end portions of the wire after interconnecting the wire of the first stent 10.

The end connection of the wire is made by a sleeve or welding, which is a known technique, so a detailed description is omitted.

The interconnection pattern portion of the wire of the second stent 20 is the same as that of the wire of the first stent 10, and only the starting origin of the second stent is the shifted origin (A1, B2) at a location shifted downward by the offset pitch Pv2 from the starting origin (A1, B1) of the first stent 10.

The starting point of each pattern is from the origin of the wire of the first stent to the end point of the vertically extending position from the origin, and the end point becomes be the starting point of another continuous pattern.

Other than the top and bottom dividing lines B1 and B13 forming the first stent 10, the top and bottom dividing lines B2 and B14 forming the second stent, and the diagonal distance 2L crossing advancement section, the intersecting wire at the intersection pin position constitutes the first stent and the second stent by hook coupling, and the first stent wire and the second stent wire are interconnected so that the same are interconnected with each other and connection of the first and second stents is implemented.

Figure 10:
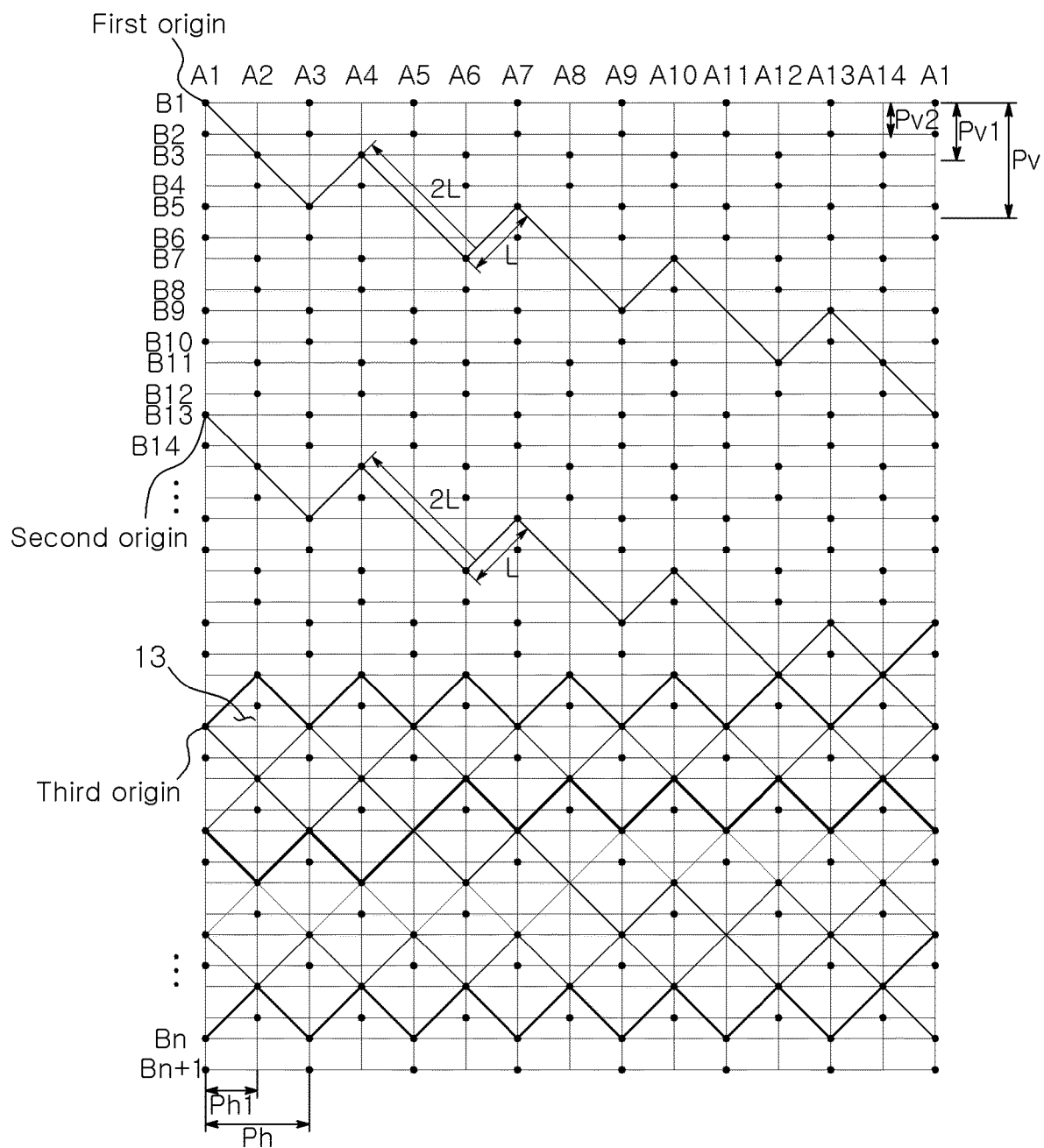
FIG. 10 is a partially omitted interconnection diagram, as another embodiment of the present invention, for manufacturing a stent extended in a longitudinal direction.
Figure 11:
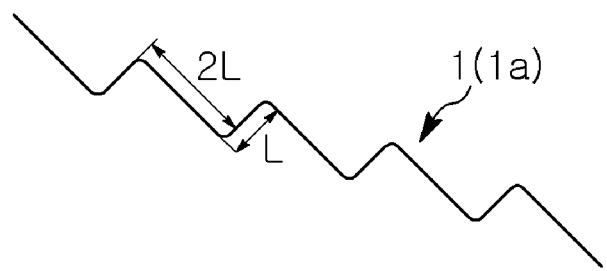
FIG. 11 is an excerpt view of first and first a pattern portions of the present invention.
Figure 12:
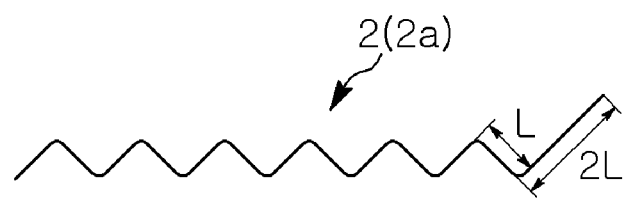
FIG. 12 is an excerpt view of second and second a pattern portions of the present invention.
Figure 13:
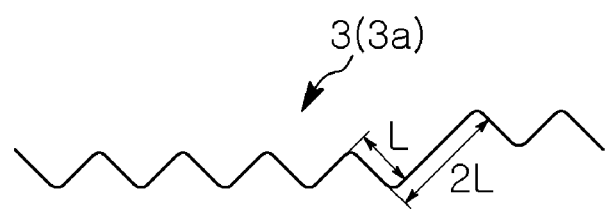
FIG. 13 is an excerpt view of third and third a pattern portions of the present invention.
Figure 14:
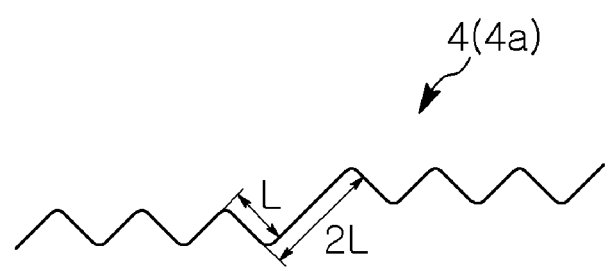
FIG. 14 is an excerpt view of fourth and fourth a pattern portions of the present invention.
Figure 15:
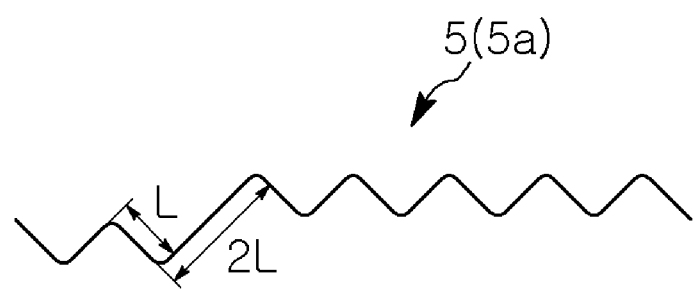
FIG. 15 is an excerpt view of fifth and fifth a pattern portions of the present invention.
Figure 16:
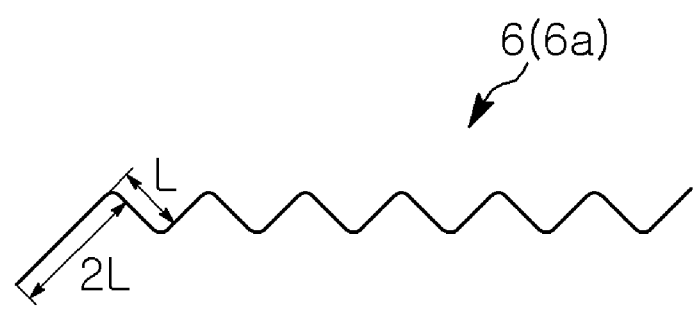
FIG. 16 is an excerpt view of sixth and sixth a pattern portions of the present invention.

As shown in FIG. 10, the present invention is also applicable to a stent extending in the Y-axis longitudinal direction.

The equator lines A1, A3, A5, A7, A9, A11, and A13 are divided by being spaced by a horizontal diagonal distance Ph of a cell forming a rhombic geometry in the X-axis direction from an arbitrary selected origin on the circumferential surface of the jig, and the equator lines A2, A4, A6, A8, A10, A12, and A14 are divided by being spaced by the horizontal diagonal distance Ph at locations apart by a length Ph1 bisecting the equator line, thereby forming 14 equator lines A1 to A14; and in the longitudinal direction of the jig, the dividing lines B3, B5, B7, B9, B11, and B13 are divided by being spaced by a length Pv1 bisecting the dividing line B1, which is the reference in the Y-axis direction from the origin, and a vertical diagonal distance Pv of a cell forming a rhombic geometry from the dividing line B1, and the dividing lines B2, B4, B6, B8, B10, B12, and B14 are divided into the same number of the dividing lines B1, B3, B5, B7, B9, B11, and B13 at locations apart by an offset pitch Pv2 from the dividing line B1, thereby forming 14 dividing lines B1 to B14, wherein the reference dividing line B1 may be formed in a multiple of the 13th dividing line so as to be located at the dividing line B13, and the bottom dividing line Bn of the multiple location of the 13th dividing line may be provided and the bottom dividing line Bn+1 of the bottom dividing line may be spaced apart from the bottom dividing line Bn by the offset pitch Pv2.

At the intersection having the equator line and the dividing line, the first pattern portion 1 is repeated to be interconnected from the origin (A1, B1) to the bottom dividing line Bn, then the second to sixth pattern portions 2 to 6 are repeated to be upwardly interconnected, whereby the extended long first stent is manufactured, and the first pattern portion 1a is repeated to be interconnected from the shifted origin (A1, B2) to the bottom dividing line Bn+1, then the second a to sixth a pattern portions 2a to 6a are repeated to be upwardly interconnected, whereby the extended long second stent is manufactured, which is a method for manufacturing an extended long stent.

A stent manufactured by the above method will be described with reference to FIGS. 3 to 8, and FIGS. 11 to 16.

In a stent formed by binding a mesh wire with a double wire, the first wire forming the first stent 10 includes: a plurality of bent loops 40 with uppermost and lowermost ends thereof being curved; a first pattern portion 1 connecting from any one origin (A1, B1) of the uppermost portion to the lowermost portion of the first stent to form a plurality of rhombic spaces 13; a second pattern portion 2 directing from an end point of the first pattern portion 1 to upward direction; and a third pattern portion 3 a fourth pattern portion 4, a fifth pattern portion 5, and a sixth pattern portion 6 directing from the second pattern portion 2 to upward direction, sequentially, whereby the interconnection of wire is implemented, and the second wire forming the second stent 20 includes: a plurality of bent loops 40 with uppermost and lowermost ends of the second stent being curved starting from an origin (A1, B2) shifted downward by being spaced by the offset pitch Pv2 from the origin of the first stent 10; a first a pattern portion 1a connecting from the shifted origin to the lowermost portion of the second stent to form a plurality of rhombic spaces 23; a second a pattern portion 2a directing from an end point of the first a pattern portion 1a to upward direction; and a third a pattern portion 3a, a fourth a pattern portion 4a, a fifth a pattern portion 5a, and a sixth a pattern portion 6a directing from the second a pattern portion to upward direction, sequentially, whereby by interconnecting wire, the second stent is spaced apart from the first stent 10 by the offset pitch Pv2 and is overlapped with the same.

Herein, in the present invention, the first to sixth pattern portions of the first stent 10 are substantially identical to the first a to sixth a pattern portions of the second stent 20.

The interconnected-wire first pattern portion 1 forming first stent 10 is bent at the intersection (A3, B5) spaced downwardly from the origin (A1, B1) by the diagonal distance 2L and bent at the intersection (A4, B3) spaced upwardly therefrom by the diagonal distance L, and bent at the intersections (A6, B7), (A7, B5), (A9, B9), (A10, B7), (A12, B11), and (A13, B9) by repeating the diagonal distances 2L and L to be interconnected to the lower most end point (A1, B13) vertically extending from the first stent origin (A1, B1).

The second pattern portion 2 is manufactured by being bent at the intersections (A2, B11), (A3, B13), (A4, B11), (A5, B13), (A6, B11), (A7, B13), (A8, B11), (A9, B13), (A10, B11), (A11, B13), (A12, B11), and (A13, B13) on the horizontal axis and interconnected to the end point (A1, B9), based on the end point (A1, B13) of the first pattern portion as a starting point.

The third pattern portion 3 is manufactured by being bent at the intersections (A2, B11), (A3, B9), (A4, B11), (A5, B9), (A6, B11), (A7, B9), (A8, B11), (A9, B9), (A10, B11), (A12, B7), (A13, B9), and (A14, B7) on the horizontal axis and interconnected to the end point (A1, B9), based on the end point (A1, B9) of the second pattern portion 2 as a starting point.

The fourth pattern portion 4 is manufactured by being bent at the intersections (A2, B7), (A3, B9), (A4, B7), (A5, B9), (A6, B7), (A7, B9), (A9, B5), (A10, B7), (A11, B5), (A12, B7), (A13, B5), and (A14, B7) on the horizontal axis and interconnected to the end point (A1, B5), based on the end point (A1, B9) of the third pattern portion as a starting point.

The fifth pattern portion 5 is manufactured by being bent at the intersections (A2, B7), (A3, B5), (A4, B7), (A6, B3), (A7, B5), (A8, B3), (A9, B5), (A10, B3), (A11, B5), (A12, B3), (A13, B5), and (A14, B3) on the horizontal axis and interconnected to the end point (A1, B5), based on the end point (A1, B5) of the fourth pattern portion as a starting point.

The sixth pattern portion 6 is manufactured by being bent at the intersections (A3, B1), (A4, B3), (A5, B1), (A6, B3), (A7, B1), (A8, B3), (A9, B1), (A10, B3), (A11, B1), (A12, B3), (A13, B1), and (A14, B3) on the horizontal axis and interconnected to the origin(A1, B1), based on the end point (A1, B5) of the fifth pattern portion 5 as a starting point.

The interconnected-wire first a pattern portion 1a forming the second stent 20 is bent at the intersection (A3, B6) spaced downwardly from the shifted origin (A1, B2) by the diagonal distance 2L and bent at the intersection (A4, B4) spaced upwardly therefrom by the diagonal distance L, and bent at the intersections (A6, B8), (A7, B6), (A9, B10), (A10, B8), (A12, B12), and (A13, B10) by repeating the diagonal distances 2L and L to be interconnected to the lower most end point (A1, B14) vertically extending from the second stent origin (A1, B2).

The second a pattern portion 2a 2 is manufactured by being bent at the intersections (A2, B12), (A3, B14), (A4, B12), (A5, B14), (A6, B12), (A7, B14), (A8, B12), (A9, B14), (A10, B12), (A11, B14), (A12, B12), and (A13, B14) on the horizontal axis and interconnected to the end point (A1, B10), based on the end point (A1, B14) of the first a pattern portion as a starting point.

The third a pattern portion 3a is manufactured by being bent at the intersections (A2, B12), (A3, B10), (A4, B12), (A5, B10), (A6, B12), (A7, B10), (A8, B12), (A9, B10), (A10, B12), (A12, B8), (A13, B10), and (A14, B8) on the horizontal axis and interconnected to the end point (A1, B10), based on the end point (A1, B10) of the second a pattern portion as a starting point.

The fourth a pattern portion 4a is manufactured by being bent at the intersections (A2, B8), (A3, B10), (A4, B8), (A5, B10), (A6, B8), (A7, B10), (A9, B6), (A10, B8), (A11, B6), (A12, B8), (A13, B6), and (A14, B8) on the horizontal axis and interconnected to the end point (A1, B6), based on the end point (A1, B10) of the third a pattern portion as a starting point.

The fifth a pattern portion 5a is manufactured by being bent at the intersections (A2, B8), (A3, B6), (A4, B8), (A6, B4), (A7, B6), (A8, B4), (A9, B6), (A10, B4), (A11, B6), (A12, B4), (A13, B6), and (A14, B4) on the horizontal axis and interconnected to the end point (A1, B6), based on the end point (A1, B6) of the fourth a pattern portion as a starting point.

The sixth a pattern portion 6a is manufactured by being bent at the intersections (A3, B2), (A4, B4), (A5, B2), (A6, B4), (A7, B2), (A8, B4), (A9, B2), (A10, B4), (A11, B2), (A12, B4), (A13, B2), and (A14, B4) on the horizontal axis and interconnected to the origin (A1, B2), based on the end point (A1, B6) of the fifth pattern portion as a starting point.

The upper portion of the sixth a pattern portion 6a is on the same horizontal axis as the starting origin of the first a pattern portion 1a, and is completed by connecting end portions of the wire after interconnecting the wire of the second stent 20.

When the horizontal diagonal distance Ph and the vertical diagonal distance Pv are in a relation of Ph=Pv, a rhombus shape is formed, all the interior angles of which are right angles and the length is Ph1=Pv1.

Alternatively, when the horizontal diagonal distance Ph and the vertical diagonal distance Pv are in a relation of Ph<Pv, the interior angles in the upper and lower positions are acute angles, and the interior angles in the left and right positions are obtuse angles, and a vertically long rhombus shape may be formed.

Alternatively, when the horizontal diagonal distance Ph and the vertical diagonal distance Pv are in a relation of Ph>Pv, the interior angles in the upper and lower positions are obtuse angles, and the interior angles in the left and right positions are acute angles, and a horizontally long rhombus shape may be formed.

No matter what the relation between the horizontal diagonal distance Ph and the vertical diagonal distance Pv is, that is, Ph=Pv, Ph<Pv, or Ph>Pv, the facing angles are always the same.

The jig 100 of the present invention using a shape memory alloy wire to interconnect a stent, includes the body 102 formed in a vertically long cylindrical shape with a circumference forming a hollow part of a stent to be manufactured, and the detachable pins 103 interconnecting the wire by being inserted at multiple split positions around the body in the X and Y-axis directions, wherein the equator lines A1, A3, A5, A7, A9, A11, and A13 are divided by being spaced by a horizontal diagonal distance Ph of a cell forming a rhombic geometry in the X-axis direction from an arbitrary selected origin on the circumferential surface of the body 102, and the equator lines A2, A4, A6, A8, A10, A12, and A14 are divided by being spaced by the horizontal diagonal distance Ph at locations apart by a length Ph1 bisecting the equator line, thereby forming the equator lines A1 to A14; and in the longitudinal direction of the jig, the dividing lines B3, B5, B7, B9, B11, and B13 are divided by being spaced by a length Pv1 bisecting the dividing line B1, which is the reference in the Y-axis direction from the origin, and a vertical diagonal distance Pv of a cell forming a rhombic geometry from the dividing line B1, and the dividing lines B2, B4, B6, B8, B10, B12, and B14 are divided into the same number of the dividing lines B1, B3, B5, B7, B9, B11, and B13 at locations apart by an offset pitch Pv2 from the dividing line B1, thereby forming dividing lines B1 to B14; and the pins 103 are inserted into some of the intersections.

The some intersections consist of locations where the first to sixth pattern portions 1 to 6 and the first a to sixth a pattern portions 1a to 6a are passed.

The first and first a pattern portions 1 and 1a are composed of the following pattern

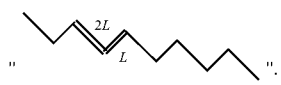

The second and second a pattern portions 2 and 2a are composed of the following pattern

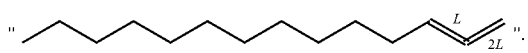

The third and third a pattern portions 3 and 3a are composed of the following pattern

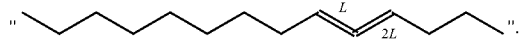

The fourth and fourth a pattern portions 4 and 4a are composed of the following pattern

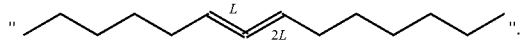

The fifth and fifth a pattern portions 5 and 5a are composed of the following pattern

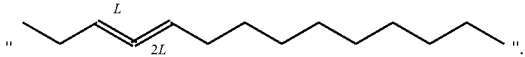

The sixth and sixth a pattern portions 6 and 6a are composed of the following pattern

Figure 17:
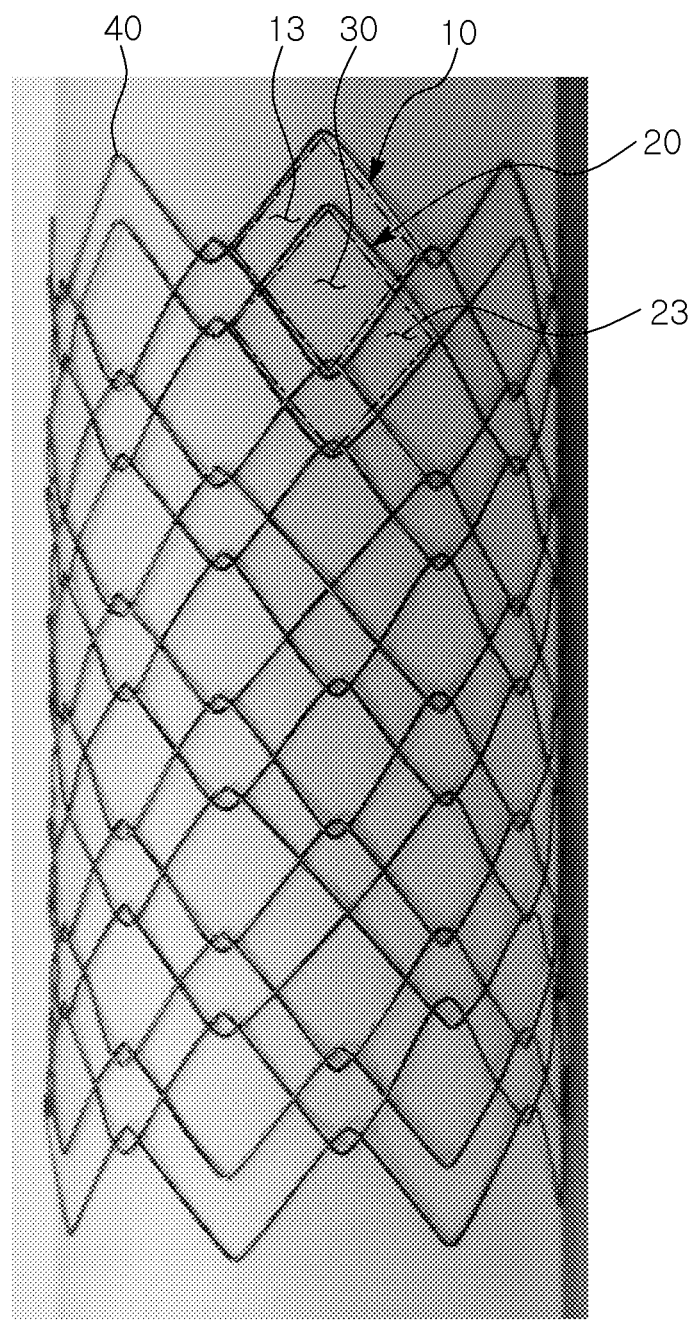
FIG. 17 is an external configuration diagram showing a stent completed by the present invention.
Figure 18:
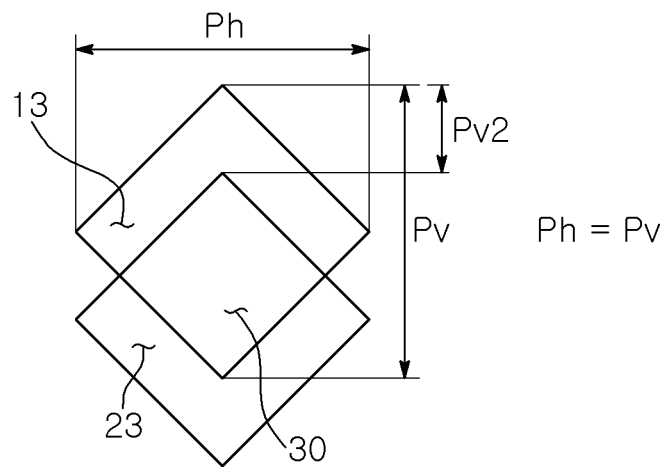
FIG. 18 is an enlarged view of an essential part of FIG. 17 of the present invention.
Figure 19:
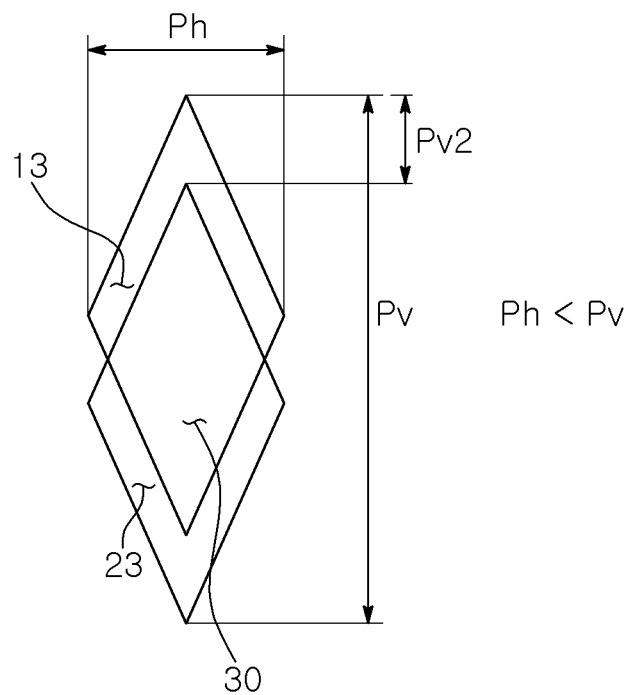
FIG. 19 is an enlarged view of an essential part of Ph<Pv state of the present invention.
Figure 20:
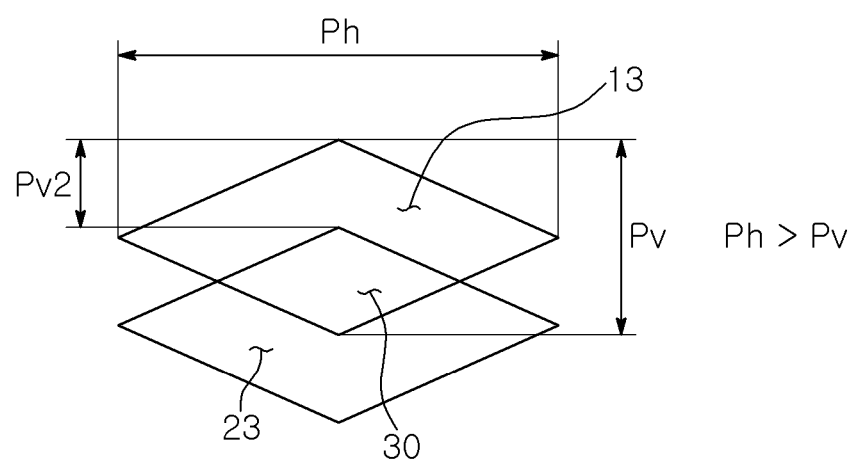
FIG. 20 is an enlarged view of an essential part of Ph>Pv state of the present invention.

The stent completed by the present invention is, as shown in FIGS. 17 and 18, configured such that cells with rhombic geometry are double-connected to each other with the offset pitch Pv2 spaced downward.

The offset pitch Pv2 can be freely adjusted within 1/2Pv and can be changed to suit the use of the stent.

When the stent of the present invention is applied to the lumen, the hooks are not concentrated or evenly arranged in a horizontal or vertical direction, even though the stent has very high conformability hooks, so it is easy to reduce the volume when the stent is integrated into the introducer.

Further, two stents are overlapped with each other to form the rhombic geometry and the facing interior angles of the rhombus are same, thereby having strong bearing capacity against external force. As a result of the test with the multi-axis stent fatigue test instrument, it was confirmed that in the expansion and shrinkage fatigue test, the stent of the present invention was able to withstand at least twice the expansion and at least six times the shrinkage over the conventional stent.

Also, since the unit cell of the first stent 10 and the unit cell of the second stent 20 are substantially not hook-coupled but are fabricated in an overlapped manner, the range of motion of the cells is largely permitted, so the size of the spaces 13 and 23 can be variably provided by using the variable offset pitch Pv2, whereby it is useful for other stent connection procedures using the overlapping space 30, and it is possible to change the shape of rhombus-shaped cell by changing the ratio of horizontal diagonal distance Ph and vertical diagonal distance Pv.

In the present invention, in the jig and in the deployment view thereof, the number of equator lines and dividing lines in the mesh wire interconnection diagram may be increased or decreased by connecting the pattern portions, whereby the circumference can be large or small and the length can be long or short, and these variations are not limited to the description of the claims. Further, those skilled in the art will appreciate that various modifications, additions and substitutions are possible, without departing from the scope and spirit of the invention as disclosed in the accompanying claims.

DESCRIPTION OF REFERENCE CHARACTERS OF IMPORTANT PARTS

1(1a)~6(6a): first to sixth pattern portions 10: first stent
13, 23: space
20: second stent 30: overlapping space
40: bent loops
A1~A14: equator line B1~B14: dividing line

The invention claimed is:

1. A stent using a shape memory alloy wire, in which interconnecting is performed by using the shape memory alloy wire and the stent has hooks and cells through direction changing of the wire and hook coupling between the wires, the stent comprising:

dividing equator lines (A1, A3, A5, A7, A9, A11, and A13) by being spaced by a horizontal diagonal distance (Ph) of a cell forming a rhombic geometry in an X-axis direction from an arbitrary selected origin on the circumferential surface of the jig, and dividing equator lines (A2, A4, A6, A8, A10, A12, and A14) by being spaced by the horizontal diagonal distance (Ph) at locations apart by a length (Ph1) bisecting the equator line, thereby forming equator lines (A1 to A14);

in a longitudinal direction of the jig, dividing dividing lines (B3, B5, B7, B9, B11, and B13) by being spaced by a length (Pv1) bisecting a dividing line (B1) as a reference in an Y-axis direction from the origin and a vertical diagonal distance (Pv) of a cell forming a rhombic geometry from the dividing line (B1), and dividing dividing lines (B2, B4, B6, B8, B10, B12, and B14) into a same number of the dividing lines (B1, B3, B5, B7, B9, B11, and B13) at locations apart by an offset pitch (Pv2) from the dividing line (B1), thereby forming dividing lines (B1 to B14);

at an intersection connecting each of the equator lines and each of the dividing lines, bending or crossing the stent wire to be in a rhombic geometry, and continuously repeating a unit cell to form a first stent (10); and vertically spacing the unit cell downward by the offset pitch (Pv2) such that a second stent (20) same as the first stent is overlapped with the same, whereby two sides provided at equiangular positions the overlapped first and second stents (10 and 20) are spaced by the offset pitch (Pv2), and a geometrically wide overlapping space (30) is formed by overlapping.

2. The stent of claim 1, wherein the first wire forming the first stent (10) includes:

a plurality of bent loops (40) with uppermost and lowermost ends thereof being curved;

a first pattern portion (1) connecting from any one origin (A1, B1) of the uppermost portion to a lowermost portion of the first stent to form a plurality of rhombic spaces (13);

a second pattern portion (2) directing from an end point of the first pattern portion (1) to an upward direction; and a third pattern portion (3), a fourth pattern portion (4), a fifth pattern portion (5), and a sixth pattern portion (6) directing from the second pattern portion (2) to an upward direction, sequentially, whereby the interconnection of wire is implemented.

3. The stent of claim 1, wherein the second wire forming the second stent (20) includes:

a plurality of bent loops (40) with uppermost and lowermost ends of the second stent being curved starting from an origin (A1, B2) shifted downward by being spaced by the offset pitch (Pv2) from the origin of the first stent (10);

a first a pattern portion (1a) connecting from the shifted origin to a lowermost portion of the second stent to form a plurality of rhombic spaces (23);

a second a pattern portion (2a) directing from an end point of the first a pattern portion (1a) to an upward direction; and a third a pattern portion (3a), a fourth a pattern portion (4a), a fifth a pattern portion (5a), and a sixth a pattern portion (6a) directing from the second a pattern portion to an upward direction, sequentially, whereby by interconnecting wire, the second stent is spaced apart from the first stent (10) by the offset pitch (Pv2) and is overlapped with the same.

4. The stent of claim 2, wherein the interconnected-wire first pattern portion (1) forming first stent (10) is bent at the intersection (A3, B5) spaced downwardly from the origin (A1, B1) by the diagonal distance (2L) and bent at the intersection (A4, B3) spaced upwardly therefrom by the diagonal distance (L), and bent at the intersections (A6, B7), (A7, B5), (A9, B9), (A10, B7), (Al2, B11), and (A13, B9) by repeating the diagonal distances (2L and L) to be interconnected to the lower most end point (A1, B13) vertically extending from the first stent origin (A1, B1).

5. The stent of claim 2, wherein the second pattern portion (2) is manufactured by being bent at the intersections (A2, B11), (A3, B13), (A4, B11), (A5, B13), (A6, B11), (A7, B13), (A8, B11), (A9, B13), (A10, B11), (A11, B13), (A12, B11), and (A13, B13) on the horizontal axis and interconnected to the end point (Al, B9), based on the end point (A1, B13) of the first pattern portion as a starting point.

6. The stent of claim 2, wherein the third pattern portion (3) is manufactured by being bent at the intersections (A2, B11), (A3, B9), (A4, B11), (A5, B9), (A6, B11), (A7, B9), (A8, B11), (A9, B9), (A10, B11), (A12, B7), (A13, B9), and (A14, B7) on the horizontal axis and interconnected to the end point (A1, B9), based on the end point (A1, B9) of the second pattern portion (2) as a starting point.

7. The stent of claim 2, wherein the fourth pattern portion (4) is manufactured by being bent at the intersections (A2, B7), (A3, B9), (A4, B7), (A5, B9), (A6, B7), (A7, B9), (A9, B5), (A10, B7), (A11, B5), (A12, B7), (A13, B5), and (A14, B7) on the horizontal axis and interconnected to the end point (A1, B5), based on the end point (A1, B9) of the third pattern portion as a starting point.

8. The stent of claim 2, wherein the fifth pattern portion (5) is manufactured by being bent at the intersections (A2, B7), (A3, B5), (A4, B7), (A6, B3), (A7, B5), (A8, B3), (A9, B5), (A10, B3), (A11, B5), (A12, B3), (A13, B5), and (A14, B3) on the horizontal axis and interconnected to the end point (A1, B5), based on the end point (A1, B5) of the fourth pattern portion as a starting point.

9. The stent of claim 2, wherein the sixth pattern portion (6) is manufactured by being bent at the intersections (A3, B1), (A4, B3), (A5, B1), (A6, B3), (A7, B1), (A8, B3), (A9, B1), (A10, B3), (A11, B1), (A12, B3), (A13, B1), and (A14, B3) on the horizontal axis and interconnected to the origin (A1, B1), based on the end point (A1, B5) of the fifth pattern portion (5) as a starting point.

10. The stent of claim 3, wherein the interconnected-wire first a pattern portion (1a) forming the second stent (20) is bent at the intersection (A3, B6) spaced downwardly from the shifted origin (A1, B2) by the diagonal distance (2L) and bent at the intersection (A4, B4) spaced upwardly therefrom by the diagonal distance (L), and bent at the intersections (A6, B8), (A7, B6), (A9, B10), (A10, B8), (A12, B12), and (A13, B10) by repeating the diagonal distances (2L and L) to be interconnected to the lower most end point (A1, B14) vertically extending from the second stent origin (A1, B2).

11. The stent of claim 3, wherein the second a pattern portion (2a) 2 is manufactured by being bent at the intersections (A2, B12), (A3, B14), (A4, B12), (A5, B14), (A6, B12), (A7, B14), (A8, B12), (A9, B14), (A10, B12), (A11, B14), (A12, B12), and (A13, B14) on the horizontal axis and interconnected to the end point (A1, B10), based on the end point (Al, B14) of the first a pattern portion as a starting point.

12. The stent of claim 3, wherein the third a pattern portion (3a) is manufactured by being bent at the intersections (A2, B12), (A3, B10), (A4, B12), (A5, B10), (A6, B12), (A7, B10), (A8, B12), (A9, B10), (A10, B12), (A12, B8), (A13, B10), and (A14, B8) on the horizontal axis and interconnected to the end point (A1, B10), based on the end point (A1, B10) of the second a pattern portion as a starting point.

13. The stent of claim 3, wherein the fourth a pattern portion (4a) is manufactured by being bent at the intersections (A2, B8), (A3, B10), (A4, B8), (A5, B10), (A6, B8), (A7, B10), (A9, B6), (A10, B8), (A11, B6), (A12, B8), (A13, B6), and (A14, B8) on the horizontal axis and interconnected to the end point (A1, B6), based on the end point (A1, B10) of the third a pattern portion as a starting point.

14. The stent of claim 3, wherein the fifth a pattern portion (5a) is manufactured by being bent at the intersections (A2, B8), (A3, B6), (A4, B8), (A6, B4), (A7, B6), (A8, B4), (A9, B6), (A10, B4), (A11, B6), (A12, B4), (A13, B6), and (A14, B4) on the horizontal axis and interconnected to the end point (A1, B6), based on the end point (A1, B6) of the fourth a pattern portion as a starting point.

15. The stent of claim 3, wherein the sixth a pattern portion (6a) is manufactured by being bent at the intersections (A3, B2), (A4, B4), (A5, B2), (A6, B4), (A7, B2), (A8, B4), (A9, B2), (A10, B4), (A11, B2), (A12, B4), (A13, B2), and (A14, B4) on the horizontal axis and interconnected to the origin (A1, B2), based on the end point (A1, B6) of the fifth pattern portion as a starting point.

16. The stent of claim 4, wherein other than the diagonal distance (2L) crossing advancement section, the intersecting wire at the intersection pin position constitutes the first stent and the second stent by hook coupling, and the first stent wire and the second stent wire are interconnected so as to be interlinked with each other, and overlapping connection of the first and second stents is implemented.

17. The stent of claim 1, wherein the first stent (10) is configured such that the equator lines (A1 to A14) and the dividing lines (B1 to B14) are formed, the reference dividing line (B1) is formed in a multiple of the 13th dividing line so as to be located at the dividing line (B13), and the bottom dividing line (Bn) of the multiple location of the 13th dividing line is provided and the bottom dividing line (Bn+1) of the bottom dividing line is spaced apart from the bottom dividing line (Bn) by the offset pitch (Pv2), and at an intersection connecting each of the equator lines and each of the dividing lines, the stent wire is bent or crossed to be in a rhombic geometry, and a unit cell is continuously repeated); and the unit cell is vertically spaced downward by the offset pitch (Pv2) such that the second stent (20) having a same structure as the first stent is overlapped therewith, whereby two sides provided at equiangular positions the overlapped first and second stents (10 and 20) are spaced by the offset pitch (Pv2), and a geometrically wide overlapping space 30 is formed by the overlapping.

18. The stent of claim 17, wherein at the intersection having the equator line and the dividing line, the first pattern portion (1) is repeated to be interconnected from the origin (A1, B1) to the bottom dividing line (Bn), then the second to sixth pattern portions (2 to 6) are repeated to be upwardly interconnected, whereby the extended long first stent is manufactured, and the first pattern portion (1a) is repeated to be interconnected from the shifted origin (A1, B2) to the bottom dividing line (Bn+1), then the second a to sixth a pattern portions (2a to 6a) are repeated to be upwardly interconnected, whereby the extended long second stent is manufactured.

* * * * *

UNITED STATES PATENT AND TRADEMARK OFFICE
CERTIFICATE OF CORRECTION

PATENT NO. : 10,806,612 B2  
APPLICATION NO. : 16/077633  
DATED : October 20, 2020  
INVENTOR(S) : Shin et al.

Page 1 of 1

It is certified that error appears in the above-identified patent and that said Letters Patent is hereby corrected as shown below:

On the Title Page

Item (73), Assignees should read:  
-- TAEWOONG MEDICAL CO., LTD., Gyeonggi-do, (KR)  
Kyong Min SHIN, Gyeonggi-do, (KR) --

Signed and Sealed this  
Twenty-fifth Day of May, 2021

Drew Hirshfeld  
*Performing the Functions and Duties of the*  
*Under Secretary of Commerce for Intellectual Property and*  
*Director of the United States Patent and Trademark Office*